(12) United States Patent
Meignant et al.

(10) Patent No.: US 6,716,454 B2
(45) Date of Patent: Apr. 6, 2004

(54) THERAPEUTIC COMBINATION OF VITAMIN AND CALCIUM IN UNITARY GALENIC TABLET FORM, A METHOD OF OBTAINING IT, AND THE USE THEREOF

(75) Inventors: Catherine Meignant, Paris (FR); Eric Stenger, Villejuif (FR)

(73) Assignee: Laboratorie Innothera, Société Anonyme, Arcueil (FR)

( * ) Notice: Subject to any disclaimer, the term of this patent is extended or adjusted under 35 U.S.C. 154(b) by 52 days.

(21) Appl. No.: 10/164,565

(22) Filed: Jun. 10, 2002

(65) Prior Publication Data
US 2002/0193355 A1 Dec. 19, 2002

Related U.S. Application Data

(63) Continuation of application No. 08/809,567, filed as application No. PCT/FR95/01053 on Aug. 4, 1995, now abandoned.

(30) Foreign Application Priority Data

Sep. 23, 1994 (FR) ............................................. 94 11381

(51) Int. Cl.$^7$ .............................. A61K 9/20; A61K 9/36; A61K 9/14; A61K 33/10; A61K 31/59

(52) U.S. Cl. ....................... 424/465; 424/479; 424/480; 424/488; 424/677; 424/687; 514/167

(58) Field of Search ......................... 514/167; 424/465, 424/479, 480, 488, 677, 678

(56) References Cited

U.S. PATENT DOCUMENTS

| | | | |
|---|---|---|---|
| 3,903,297 A | | 9/1975 | Robert ........................ 424/305 |
| 5,104,864 A | * | 4/1992 | DeLuca et al. .............. 514/167 |
| 5,158,944 A | | 10/1992 | Makino et al. .............. 514/167 |
| 5,443,850 A | * | 8/1995 | Thys-Jacobs ................ 424/682 |
| 5,502,224 A | * | 3/1996 | Eugster et al. .............. 552/653 |

FOREIGN PATENT DOCUMENTS

| | | |
|---|---|---|
| EP | 0 413 828 | 2/1991 |
| EP | 0 581 676 A2 | 2/1994 |
| EP | 0 785 769 | 7/1997 |
| WO | 92/19251 | 11/1992 |

OTHER PUBLICATIONS

Ivey. M; "Nutritional Supplement Minera and Vitamin Products"; Handbook of Nonprescription Drugs; Fifth Edition; pp 134–162, 1977.*

Aloia et al.; Calcitriol in the Treatment of Postmenopausal Osteoporosis; Amer. J. Of Med., vol. 84 pp. 401–408 (1988).*

Garr et al., "Direct compression characteristics of xylitol", International Journal of Pharmaceutics, 64 (1990), p. 223–226.

Dills, Jr., "Sugar Alcohols as Bulk Sweeteners", Department of Chemistry, Southeastern Massachusetts University, North Darmouth, Mass., Annu. Rev. Nutr., 9, 1989, 161–86.

Mosk, Med. Inst., 61, 1968, 128–32 (English Language Abstract).

Physicians' Desk Reference For Nonprescription Drugs, 1993, item "SO–CAL 500+D Tablets".

Physicians' Desk Reference For Nonprescription Drugs, 1992, item "DICAL–D Tablets–Wafers."

Physicians'Desk Reference For Nonprescription Drugs, 1993, item "CALTRATE 600 + Vitamin D".

Vidal 1994, item "Calciprat 750 mg" (translated in part).

OS–CAL 500+D, Physicians Desk Reference; 14 Edition; 1993.

DICAL–D Tablets; Physicians Desk Reference; 46 Edition, 1992.

CALCIPRAT 750; Vidal 1994.

Denoel et al.; Preparation de la Poudre a Comprimer; Pharmacie Galentique; Les Presses Universitaires de Liege; 1971; PP 34–59.

Extracts Physicians Desk Reference; 46 Edition; 1992.

Chapuy et al.; Vitamin $D_3$ and Calcium to Prevent Hip Fractures in Elderly Women; The New England Journal of Medicine; vol. 327, No. 23; pp. 1637–1642; 1992.

Supplementation with Vitamin $D_3$ and Calcium Prevents Hip Fractures in Elderly Women; Nutrition Reviews, vol. 51, No. 5 pp. 183–185; 1992.

Chapuy et al.; Effect of Calcium and Cholecalciferol Treatment for Three Years on Hip Fractures in Elderly Women; BMJ; vol. 308; 1994; pp. 1081–1082.

Hir; Abrégé de Pharmacie Galénique; 1974; Formes Pharmaceutiques; PP 204–209.

Denoel et al.; Pharmacie Galentque; Preparation de la Poudre a Comprimer; Les Presses Universitaires de Liege; 1971 pp. 34–59.

Meunier et al.; Biochemical Response to Combined Vitamin D3 and Calcium Supplementation in Elderly People with Vitamin D Insufficiency; Ninth Workshop on Vitamin D; Orlando, FL.; 1994.

Riggs et al.; The Prevention and Treatment of Osteoporosis; The New England Journal of Medicine; 1992; vol. 327, No. 9; PP 620–627.

(List continued on next page.)

Primary Examiner—Theodore J Criares
(74) Attorney, Agent, or Firm—Jacobson Holman PLLC

(57) ABSTRACT

The therapeutic combination comprises as its associated active ingredients calcium in elemental form and at least one vitamin D. It also contains at least one dry and moist binder combined in synergistic quantity with at least one diluant, at least one binder, and at least one lubricant, at least one of said diluant and said binder being a sweetening agent. Advantageously, the ratio of calcium in elemental form to vitamin D, expressed in mg of elemental Ca per IU of vitamin D lies in the range 1 to 1.5, and preferably in the range 1.2 to 1.3.

15 Claims, No Drawings

OTHER PUBLICATIONS

Budden; Osteoporosis in Geriatrics; Can Pharm J; PP 276–278; 1985.

Chapuy et al.; Effect of Calcium and Cholecalciferol Treatment For Three Years on Hip Fractures in Elderly Women; BMJ; vol. 308 1994; PP 1081–1082.

Handbook of Sweeteners; Blackie and Son., LTD.; 1991.

Ullmanns Encyklopädie der Technischen Chemie; PP 156; 1979 Verlag Chemie.

Müller; Gutachterliche Stellungnahme Zur Patentanmeldung PCT/FR 95/01053; Pharmazeutisches Institut.

Müller; Prise de Position D'Expert Relative a la Demande de Brevet PCT/FR 95/01053; Traduit de L'Allemand; Institut Pharmaceutique.

Grundstoffe und Verfahren der Arzneibereitung; Ferdinand Enke Verlag Stuttgart; 1960; PP 116.

The Theory and Practice of Inductrial Pharmacy; Second Edition; Lea & Febiger; 1976; PP 339–340.

Pharmaceutical Dosage Forms; vol. 1; Marcel Dekker, Inc. 1980; PP 289–337.

Pharmaceutical Sciences; 1990; Mack Publishing Company; PP 1634–1638.

* cited by examiner

THERAPEUTIC COMBINATION OF VITAMIN AND CALCIUM IN UNITARY GALENIC TABLET FORM, A METHOD OF OBTAINING IT, AND THE USE THEREOF

This application is a continuation of U.S. application Ser. No. 08/809,567, filed Jun. 19, 1997, now abandoned, which is a 371 of PCT/FR95/01053, filed Aug. 4, 1995.

The present invention relates to a novel therapeutic combination of vitamin and calcium, to a method of obtaining it, and to the use thereof.

Numerous combinations of vitamin and calcium are known for treating various diseases.

The therapeutic effects associated with simultaneous administration of calcium and of vitamin D are well known, as described, for example, in articles by Marie C. Chapuy et al. "Effect of calcium and cholecalciferol treatment for three years on hip fractures in elderly women", British Medical Journal, 308, pp. 1081–1082 (Apr. 23, 1994); Marie C. Chapuy et al. "Vitamin D3 and calcium to prevent hip fractures in elderly women", New England Journal of Medicine, 327, pp. 1637–1642 (Dec. 3, 1992); and in the article entitled "Supplementation with vitamin D3 and calcium prevents hip fractures in elderly women", Nutrition Reviews, Vol. 51, 6, pp. 183–185.

Those articles also show up the variability of the therapeutic effects of the combination as a function of calcium dosage and of vitamin D dosage, with an optimum daily dose lying around 1000 mg to 1200 mg of elemental calcium and 800 IU of vitamin D3 for the purpose of preventing and treating osteoporosis.

Calcium and vitamin D are generally administered to the patient simultaneously, but in distinct forms, e.g. tablets of a calcium salt and drops of vitamin D.

Both vitamin D and the salts of calcium that are acceptable from the pharmacological point of view present characteristics that are highly specific from the galenic point of view (see in particular EP-A-0 413 828 which relates to a stabilized preparation of vitamin D3 for potentializing the stability of the active ingredient), which leads to them being packaged in separate forms.

However that makes it difficult to ensure that absolute and relative dosages of calcium and of vitamin D are complied with, and thus that the treatment is carried out correctly, particularly if it takes place over a long period.

Proposals have already been made to associate calcium and vitamin D in the same form, e.g. in WO-A-94 06435 (a gynecological treatment method using, in particular, a combination of vitamin D and calcium), in WO-A-92 19251 (a combination of vitamin D with calcium for treating osteoporosis, in particular in drinkable form), in EP-A-0 197 514 (a pharmaceutical composition comprising a parathyroid hormone or a physiologically active fragment thereof in combination with hydroxylated vitamin D or a non-toxic calcium salt for increasing bone mass), or indeed in DE-A-42 12 122 (a low calorie element based on proteins, a calcium salt, and vitamin D).

However, in those known forms, the proportions of calcium and of vitamin D are generally rather far from the desirable optimal proportions as indicated in particular in the above-specified literature.

Those known forms also often correspond more to vitamin and calcium supplements (food supplements or "OTC" specialities sold without medical prescription) than to real pharmaceutical specialities for therapeutic purposes intended to prevent or treat diseases such as osteoporosis with precise dosage.

At present there exists a need to be able to dispose of an combination of vitamin and of calcium including in a single form an optimal relative dose of calcium and of vitamin D, most particularly for preventing and treating osteoporosis.

However, because of the nature of the available calcium salts that are acceptable from the pharmaceutical point of view, it is relatively difficult to associate calcium in elemental form with vitamin D in certain specific dosages. This is particularly true if it is desired to obtain tablets by a direct compression manufacturing method. The constraints on the active ingredients, in particular the calcium in elemental form and the form of the vitamin D, then prevent direct implementation.

The present invention solves the above-mentioned problems by proposing a therapeutic combination of vitamin and calcium in unitary galenic tablet form, comprising as associated active ingredients, at least one vitamin D and calcium in elemental form, the combination being characterized in that it further includes at least one dry and moist binder combined in synergistic quantity with at least one diluant, at least one binder, and at least one lubricant, at least one of said diluant and said binder being a sweetening agent.

The present invention also provides a method of obtaining a therapeutic combination of vitamin and calcium in unitary galenic tablet form comprising as associated active ingredients calcium in elemental form and at least one vitamin D, the method being characterized in that it consists:

a) in granulating the calcium in elemental form with a dry and moist binder;

b) premixing the vitamin D with a sweetening binder in a separate step;

c) mixing in another separate step a sweetening diluant, an additional sweetening binder, and flavoring with the products of steps a) and b), while also adding a lubricant; and d) optionally compressing the mixture in a rotary press.

The invention also relates to the use of the novel therapeutic combination of vitamin and calcium for treating osteoporosis.

The invention also relates to the following characteristics:

the ratio of calcium in elemental form to vitamin D, expressed in mg of elemental Ca per IU of vitamin D, lies in the range 1 to 1.5, and preferably in the range 1.2 to 1.3;

the calcium in elemental form comes from a calcium salt selected from calcium carbonate, calcium pidolate, calcium lactate, calcium citrate, calcium gluconate, calcium chloride, calcium glucoheptonate, calcium glycerophosphate, and calcium phosphate;

the vitamin D is selected from vitamin D2 or ergocalciferol, vitamin D3 or cholecalciferol, or a mixture thereof;

the tablet belongs to the group comprising tablets for biting, cleavable tablets, chewable tablets, dispersible tablets, and tablets for a drinkable suspension;

at least one of said diluant and said sweetening binder is a flavoring agent suitable for improving the taste characteristics of the combination, advantageously a polyol, in particular selected from mannitol, sorbitol, xylitol, and maltitol;

the dry and moist binder is selected from a cellulose, maltodextrin, and polyvinylpyrrolidone;

the lubricant is selected from magnesium stearate, steric acid, hydrogenated castor oil, hydrogenated cotton oil, and glycerol behenate;

the combination also includes a flavoring agent and/or an acidifying agent and/or an additional sweetening agent selected from sodium saccharinate, sodium cyclamate, and aspartame; and the combination of vitamin and calcium complies with the following general formula:

| | |
|---|---|
| Calcium (carbonate) | 1250 mg |
| (Corresponding to elemental calcium | 500 mg) |
| Cholecalciferol | 4 mg* |
| Xylitol | 661 mg |
| Sorbitol | 500 mg |
| Polyvinylpyrrolidone | 45 mg |
| Flavoring (lemon, orange, etc.) | 20 mg |
| Magnesium stearate | 20 mg |
| (*Vitamin D3 dosed at 100,000 IU/g) | |
| Said formula corresponding to a finished tablet weighing | 2500 mg |

Various characteristics and advantages of the present invention appear from an example below.

In this example, the combination of the invention is in the form of a tablet for biting having the following formula (for a final tablet weighing 2500 mg):

| | |
|---|---|
| Calcium (carbonate) | 1250 mg |
| (Corresponding to elemental calcium | 500 mg) |
| Cholecalciferol | 4 mg* |
| Xylitol | 661 mg |
| Sorbitol | 500 mg |
| Polyvinylpyrrolidone | 45 mg |
| Flavoring (lemon, orange, etc.) | 20 mg |
| Magnesium stearate | 20 mg |
| (*Vitamin D3 dosed at 100,000 IU/g) | |

The calcium carbonate is of the SCORALITE 1B® type from SCORA; it is in the form of a white powder of very fine grains having a mean diameter of about 12 micrometers, and high density (d=1.3 g/cm$^3$ approx.) that flows poorly and that is relatively unsuitable for being compressed.

The vitamin D is cholecalciferol (type 100 CWS®, from ROCHE); it is in the form of a granular powder having a mean diameter of 200 micrometers approx., it is yellowy in color, and dosed at 100,000 IU per gram.

The presence of DL-α-tocopherol (about 0.2% w/w of vitamin E) gives a high degree of stability thereto and prevents it from oxidizing.

The sweetening and diluting agent used in the invention is preferably xylitol of the XYLITAB 300® type from FINNSUGAR. Such xylitol is a sweet-tasting polyol (equivalent to that of sucrose, giving an agreeable sensation of freshness in the mouth, it is not a carcinogen and provides very few calories (2.4 Kcal/g as compared with 4 Kcal/g for sucrose). The agreeable sensation ensures that the treatment is better complied with by the patient. The xylitol used has compressibility properties that are better than those of standard xylitol.

The tablet is in the form of a white crystalline granular powder having a mean diameter of 250 micrometers.

The sweetening agent and binder used in the present invention is, in particular, sorbitol (of the NEOSORB P 60 W® type, from ROQUETTE). This polyol is in the form of a white granular powder having a mean diameter of 200 micrometers and it possesses excellent binding and compression properties. Sorbitol has a sweet flavor (70% that of sucrose), it is not a carcinogen, and it provides few calories (2.4 Kcal/g).

The binder of the present invention is preferably polyvinylpyrrolidone (of the KOLLIDON K 30® type, from BASF); it is in the form of a granular whitish powder and possesses very great binding properties in moist grains. The value of the constant K characterizes soluble polyvinylpyrrolidones and depends on their relative solubility.

The flavoring agent is in particular lemon flavoring (SBI); it is in the form of a fine yellowy powder made up of essential oils atomized on maltodextrin. Numerous tests performed in implementing the present invention and comparing different flavorings have shown that lemon flavoring is entirely suitable for masking the chalky taste of calcium carbonate and that it associates agreeably with the sensation of freshness provided by the xylitol.

The lubricant is generally a magnesium stearate in the form of a whitish fine powder serving to avoid the phenomenon whereby the matrices of the tablet-making presses jam when the vitamin and calcium combination of the present invention is provided in tablet form.

The quantity of elemental calcium per dose is preferably 500 mg, which corresponds to 1250 mg of calcium carbonate.

The quantity of cholecalciferol per dose is 4 mg, which corresponds to 400 IU of vitamin D3 at 100,000 IU/g. In practice, the quantity of cholecalciferol per tablet depends on the dosage of the raw material used.

These doses correspond in particular to optimum dosage as given in the above-mentioned publications both with respect to absolute value (daily doses of calcium and of vitamin D3, respectively) and to relative doses (ratio of calcium to vitamin of about 1.25 mg of elemental Ca per IU of vitamin D).

Numerous tests on formulations of this example have enabled the quantities of the various excipients to be optimized.

In order to obtain a tablet for biting that has the most agreeable taste possible, the contribution of dry binder and of moist medium combined in synergistic quantity with at least the sweetening diluant, at least the sweetening binder, and at least the lubricant, must be considerable. For a tablet, that means its weight will generally be 2500 mg.

In certain implementations of the present invention, the quantity of xylitol used is about 661 mg, corresponding to the quantity that needs to be incorporated in order to obtain best masking of the calcium carbonate taste without simultaneously reducing the compressibility of the mixture, given that the compression properties of xylitol are average.

The sorbitol is used at about 500 mg since that is the quantity which needs to be incorporated in order to obtain good reproducibility of the breaking strength range, a parameter which is critical for tablets that are to be bitten. A higher quantity, to the detriment of xylitol, would reduce the taste quality of the tablet.

The polyvinylpyrrolidone is used at a rate of about 45 mg during moist granulation of the calcium carbonate, a portion (20 mg) being mixed dry with the calcium carbonate while the remainder (25 mg) is used in a solution at 10% in cold demineralized water. A polyvinylpyrrolidone content of less than 40 mg leads to the grains of calcium carbonate being excessively friable. A greater quantity does not give rise to any real benefit.

The quantity of lemon flavoring is about 20 mg, with that being the quantity required to impart satisfactory flavor to the tablet. Small variations in this quantity (±3 mg) give rise to practically no change in the final taste.

The quantity of magnesium stearate is about 20 mg. That is the quantity required for obtaining satisfactory lubrication during compression. A smaller quantity, about 15 mg, would give rise to a jamming phenomenon, whereas a larger quantity, 25 mg, would tend to reduce the hardness of the tablet and would run the risk of changing its taste.

The physical characteristics of the elements making up the combination of vitamin and calcium of the present invention are described below.

Calcium carbonate has zero flow and its apparent density ($g/cm^3$) is about 1.28 to 1.35 for a residual moisture content of 0.1%. The cholecalciferol D3 vitamin in the form of a concentrate in powder form has a flow of 6 seconds for 100 g of powder, an apparent density of 0.73 $g/cm^3$, a residual moisture content of 6.4%, and a dosage in IU/g of 100,000.

The xylitol has zero flow, and apparent density of about 0.68 $g/cm^3$ to 0.69 $g/cm^3$, and residual moisture content of 0.2% to 0.3%.

Sorblitol has flows in the range 4 to 5 seconds for 100 g of powder, an apparent density of 0.71 $g/cm^3$ to 0.73 $g/cm^3$, and a residual moisture content of 0.5% to 0.8%.

The preferred steps in implementing the method of obtaining the combination of vitamin and calcium of the present invention are described below.

Initially, moist granulation of the calcium carbonate is performed.

In this implementation, the calcium carbonate and the polyvinylpyrrolidone are sifted through a vibrating sifter provided with a screen having an appropriate mesh size; these powders are put into a mixer and they are mixed together for a short time at an appropriate speed. Polyvinylpyrrolidone solution is added in successive stages. Granulation is performed until a moist mass is obtained making it possible to perform a following precalibration step.

Precalibration is performed on a granulator provided with a screen having an appropriate mesh size.

The resulting product is dried on a fluidized air bed and is allowed to cool.

The loss of weight on drying is determined and calibration on a screen of appropriate mesh size is performed.

In parallel, vitamin D3 is premixed, and after sifting, it is mixed with sorbitol in a mixer for an appropriate length of time at a suitable speed of rotation. Thereafter, the other ingredients are mixed in, sifting the xylitol, the sorbitol, and the flavoring over a vibrating sifter fitted with a screen having an appropriate mesh size. These three ingredients are mixed with the premixture of vitamin D3 and sorbitol in a mixer at an appropriate speed. Thereafter, the granulated calcium carbonate is inserted and mixing is continued for the required length of time at the appropriate speed.

The magnesium stearate is sifted on a vibrating sifter provided with a screen having an appropriate mesh size, and then the entire mixture is mixed in a mixer.

The above mixture is then compressed in a press while regularly monitoring weight uniformity and breaking strength. The times required for mixing, the speeds of rotation, and the mesh sizes of the sifters are conventional and are well known to the person skilled in the art.

Thus, the present invention makes it possible to obtain a combination of vitamin and calcium containing 500 mg of elemental calcium and 4 mg of vitamin D3 per dose, which combination is specifically in the form of a tablet for biting that is of agreeable taste and of a hardness matched to the patients.

More particularly, by way of non-limiting example, doses will generally be used in the following ranges: calcium in elemental form about 500 mg to about 1500 mg; vitamin D or a mixture of vitamins D, about 3.5 mg to about 12 mg. Such a combination of vitamin and calcium, in particular in tablet form, contains neither sugar nor sodium.

However other galenic forms are possible.

It is thus possible to provide a cleavable tablet (for swallowing) having the following formula for a 1.60 g tablet:

| | |
|---|---|
| Calcium carbonate | 1.250 g |
| Vitamin D3 | 0.004 g |
| Microcrystalline cellulose | 0.236 g |
| Polyvinylpyrrolidone | 0.040 g |
| Magnesium stearate | 0.020 g |

In general, to implement tablets of a type for chewing, calcium carbonate is used. Other salts such as calcium triphosphate could be used, but they are less well absorbed by the body, which means that the quantities would need to be adapted accordingly (for a given quantity of absorbed elemental calcium, it is necessary to use about 1.2 g of calcium triphosphate for 1 g of calcium carbonate).

What is claimed is:

1. A therapeutic combination of vitamin and calcium comprising, in unitary galenic form of a tablet for biting, and in the absence of sodium and sugar, a) as combined active ingredients, calcium and at least one vitamin D, and b) at least one first binder, which first binder is dry and moist, combined in effective quantity with at least one diluent, at least one second binder, and at least one lubricant at a weight ratio based on elemental calcium of at least 0.08., wherein at least one of said diluant and said second binder is a polyol sweetening agent, and wherein the calcium and vitamin D are present at a ratio, based on mg of elemental Ca per IU of vitamin D, of 1–1.5.

2. A combination according to claim 1, wherein said ratio of calcium to vitamin D is 1.2–1.3.

3. A combination according to claim 1, wherein said second binder is a polyol sweetening agent.

4. A combination according to claim 3, wherein said second binder is selected from the group consisting of mannitol, sorbitol, xylitol, and maltitol.

5. A combination according to claim 1, wherein the calcium is present as a calcium salt selected from the group consisting of calcium carbonate, calcium pidolate, calcium lactate, calcium citrate, calcium gluconate, calcium chloride, calcium glucoheptonate, calcium glycerophosphate, and calcium phosphate.

6. A combination according to claim 1, wherein the vitamin D is selected from the group consisting of ergocalciferol, cholecalciferol, and a mixture thereof.

7. A combination according to claim 1, wherein said first binder is selected from the group consisting of a cellulose, maltodextrin, and polyvinylpyrrolidone.

8. A combination according to claim 1, wherein said lubricant is selected from the group consisting of magnesium stearate, stearic acid, hydrogenated castor oil, hydrogenated cotton oil, and glycerol behenate.

9. A combination according to claim 1, further comprising a flavoring agent.

10. A combination according to claim 1, further comprising an acidifying agent.

11. A combination according to claim 1, further comprising a sweetening agent selected from the group consisting of sodium saccharinate, sodium cyclamate, and aspartam.

12. A combination according to claim 1, consisting of:

| | |
|---|---|
| calcium carbonate | 1250 mg, |
| corresponding to 500 mg elemental calcium; | |
| cholecalciferol dosed at 100,000 IU/g | 4 mg; |
| xylitol | 661 mg; |
| sorbitol | 500 mg; |
| polyvinylpyrrolidone | 45 mg; |
| flavoring | 20 mg; and |
| magnesium stearate | 20 mg; |
| corresponding to a finished tablet weighing | 2500 mg. |

13. A method of obtaining a therapeutic combination of vitamin and calcium in a unitary galenic tablet for biting, said tablet comprising as associated active ingredients calcium and at least one vitamin D, comprising the steps of:

a) granulating a calcium salt with a dry and moist binder, effecting a granulate;

b) mixing the vitamin D with a sweetening binder, effecting a mix;

c) mixing a sweetening diluant, a second sweetening binder, a lubricant, and flavoring with the granulate and the mix, effecting a mixture; and d) compressing the mixture into the tablet in a rotary press.

14. A method of treating osteoporosis comprising administering to a patient an effective amount of the therapeutic combination according to claim 1.

15. A therapeutic combination of vitamin and calcium in unitary galenic tablet form consisting of:

| | |
|---|---|
| calcium carbonate | 1250 mg, |
| corresponding to 500 mg elemental calcium; | |
| cholecalciferol dosed at 100,000 IU/g | 4 mg; |
| xylitol | 661 mg; |
| sorbitol | 500 mg; |
| polyvinylpyrrolidone | 45 mg; |
| flavoring | 20 mg; and |
| magnesium stearate | 20 mg; |
| corresponding to a finished tablet weighing | 2500 mg. |

* * * * *